(12) United States Patent
Lu et al.

(10) Patent No.: US 9,872,747 B2
(45) Date of Patent: Jan. 23, 2018

(54) WOVEN FIBER OPTICS DENTAL POST

(71) Applicants: ILUMI Sciences Inc., Chantilly, VA (US); Luke Lu, San Diego, CA (US)

(72) Inventors: Luke Lu, San Diego, CA (US); Kuan-Yu Lu, Taipei (TW); Toshihiro Tokizawa, Tokyo (JP); I-Ching Lu, Taipei (TW)

(73) Assignees: ILUMI SCIENCES INC., Chantilly, VA (US); Luke Lu, San Diego, CA (US)

( * ) Notice: Subject to any disclaimer, the term of this patent is extended or adjusted under 35 U.S.C. 154(b) by 179 days.

(21) Appl. No.: 14/703,844

(22) Filed: May 4, 2015

(65) Prior Publication Data
US 2016/0324606 A1    Nov. 10, 2016

(51) Int. Cl.
*A61C 5/08* (2006.01)
*A61C 13/30* (2006.01)
*A61C 13/15* (2006.01)

(52) U.S. Cl.
CPC .......... *A61C 13/30* (2013.01); *A61C 19/003* (2013.01)

(58) Field of Classification Search
CPC .......... A63B 19/00–19/10; A63B 13/00–13/34
USPC ............................................. 433/215–228.1
See application file for complete search history.

(56) References Cited

U.S. PATENT DOCUMENTS

| | | | | |
|---|---|---|---|---|
| 4,504,113 A | * | 3/1985 | Baak | C03C 25/104 385/128 |
| 4,505,541 A | * | 3/1985 | Considine | G02B 6/443 174/136 |
| 4,515,435 A | * | 5/1985 | Anderson | G02B 6/4415 385/103 |
| 5,326,263 A | * | 7/1994 | Weissman | A61C 5/50 433/220 |
| 5,871,359 A | * | 2/1999 | Billet | A61C 13/30 433/220 |
| 5,915,970 A | * | 6/1999 | Sicurelli, Jr. | A61C 13/30 433/220 |

* cited by examiner

*Primary Examiner* — Stephen R Crow
*Assistant Examiner* — Garrett Atkinson
(74) *Attorney, Agent, or Firm* — Leong C. Lei

(57) ABSTRACT

A woven fiber optics dental post includes a post body and a woven fiber component. The post body includes a post face, an irradiation receiving portion, and a bottom. The woven fiber component is provided within the post body. The woven fiber component is formed by intertwining a plurality of fiber optics members. A light receiving end portion and a light emitting end portion are respectively composed of a plurality of light receiving ends and light emitting ends of the fiber optics members. The light receiving end portion is appeared on the irradiation receiving portion of the post body for having the woven fiber component receiving a light irradiated at the irradiation receiving portion, and the light emitting end portion is appeared on the post face and/or the bottom of the post body for having the light received by the woven fiber component transmitting to the light emitting end portion to be emitted out of the post face and/or the bottom. Thereby the structure strength and the intensity and the uniformity of the light emitted from the woven fiber optics dental post can be enhanced.

8 Claims, 14 Drawing Sheets

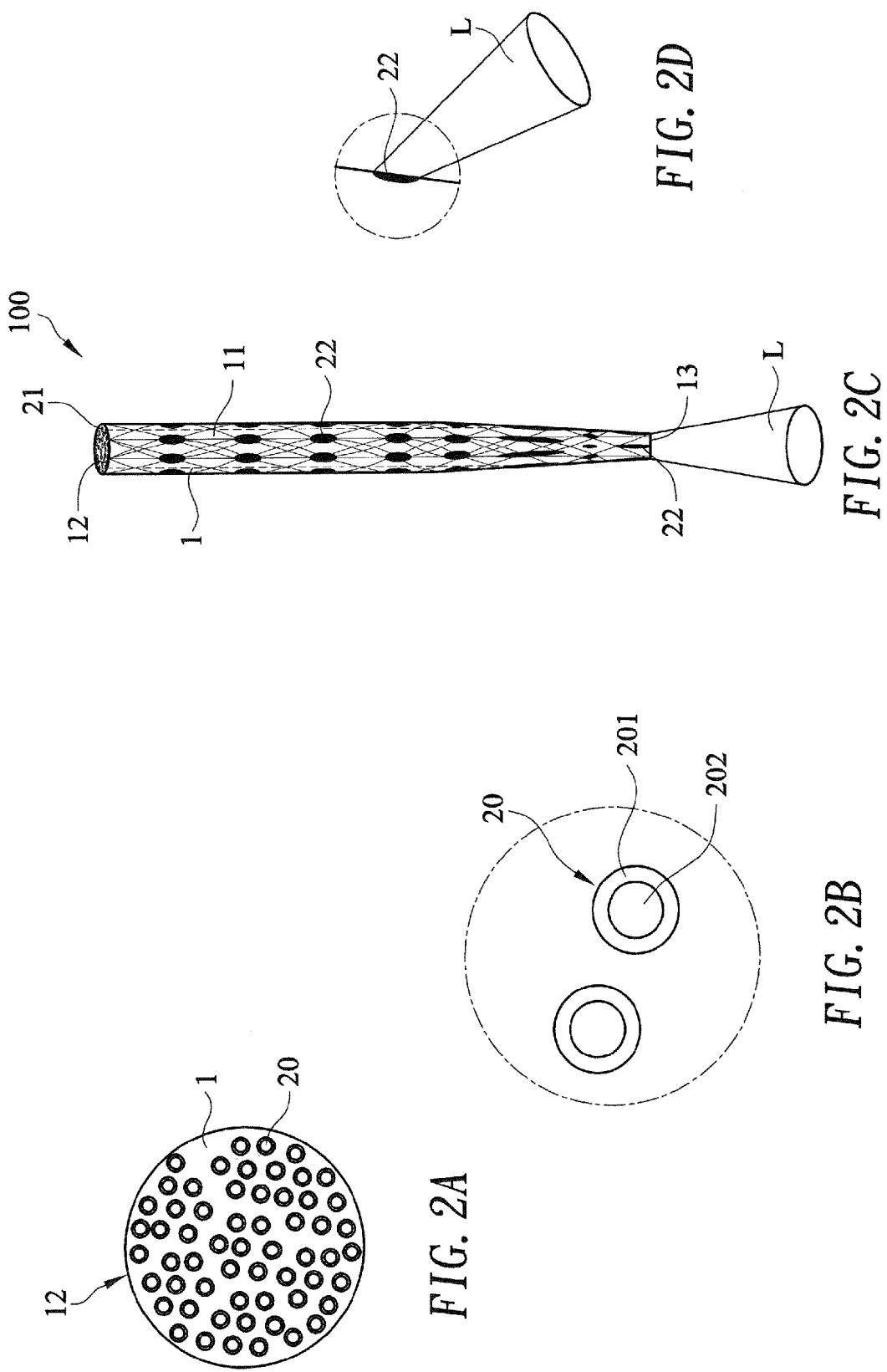

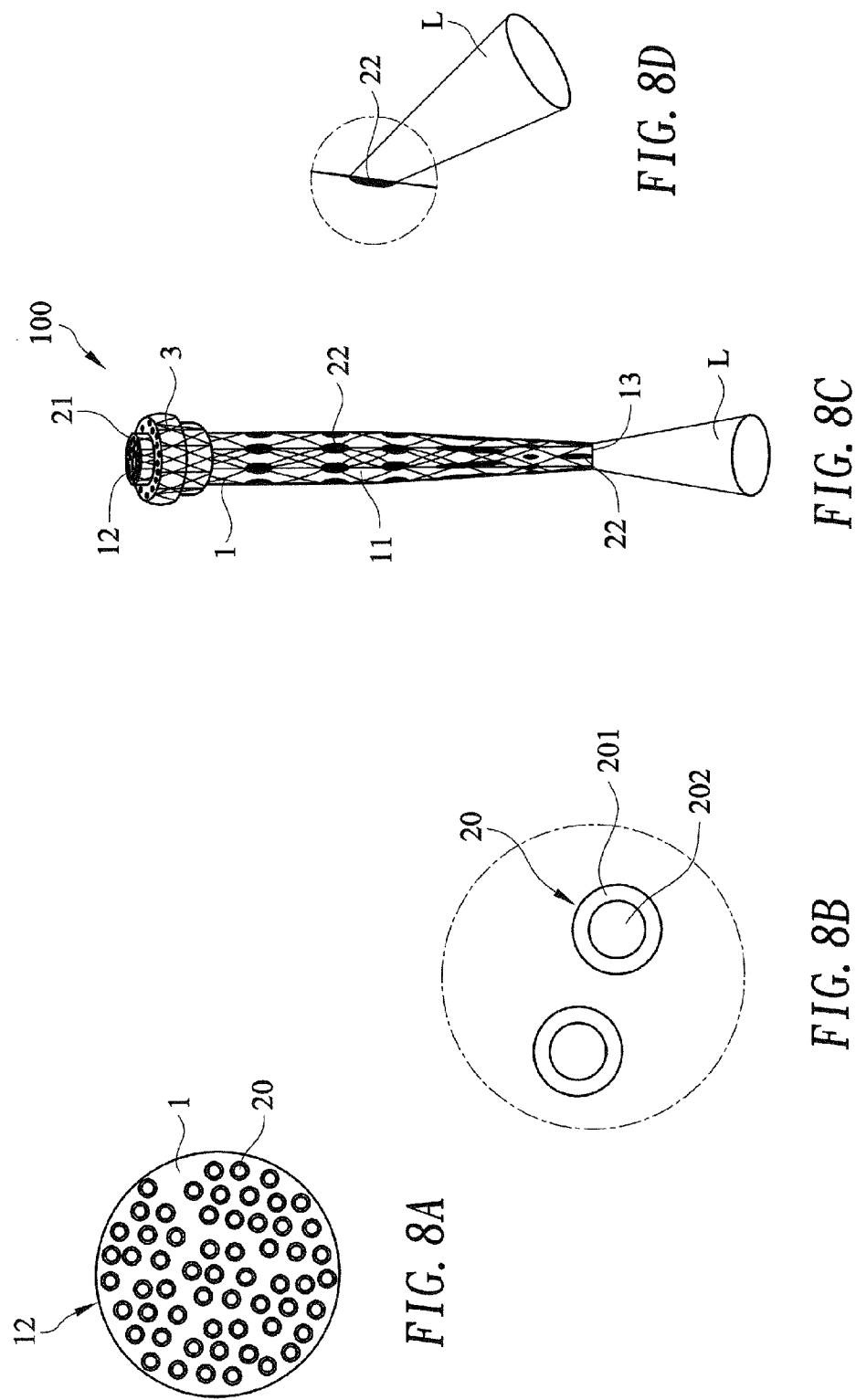

WOVEN FIBER OPTICS DENTAL POST

BACKGROUND OF THE INVENTION (a) Technical Field of the Invention

The present invention relates to a dental post, and more particularly to a woven fiber optics dental post.

(b) Description of the Prior Art

After tooth root canal treatment, the tooth is structurally fragile due to tooth canal hole or empty space. In order to improve the strength of the tooth, dental post is used to be implanted into the root canal to support and build up the core for the dental prosthesis, such as artificial tooth and dental mouthpiece. Dental posts are generally divided into metal post and fiber post. Metal post is criticized since it may cause the all-ceramic crown looking gray. In addition, since the metal post is too hard, it may also cause root canal fracture because it indirectly applies force on the root canal when occluding teeth. For the reason mentioned above, the demand for fiber post continuously increases in the recent years. The fiber post is made of fiber reinforced polymer, when occluding teeth, it may be bent along with the root canal, so that the root canal fracture causing by factors of the hard metal post can be prevented. Moreover, the fiber post does not include the mental ingredient, so that the problem of allergy and corrosion will not occur. Furthermore, the color of fiber post is similar with that of tooth, so that it is most suitable for the all-ceramic crown in view of the aesthetic requirement.

Clinically, adhesives are commonly used to glue the fiber post by dentists. Photocurable adhesive is advantageous for saving treatment time due to short curing time. However, if the polymerization of the photocurable adhesive is incomplete, its physical properties may become worse and thus the problem of bad adhesion efficacy, bad attrition resistance, and the bio-incompatibility due to microleakage, which result in clinical treatment failure, may be occur. In the recent years, literatures show that polymerization degree of the photocurable adhesive has a positive correlation with the light intensity. However, it is need to improve the weak light intensity due to bad light-guiding efficacy of the conventionally posts, which causes incomplete polymerization of the photocurable adhesive.

Accordingly, it is an important issue to enhance the light intensity and to maintain the structure strength of the dental post.

SUMMARY OF THE INVENTION

The present invention provides a woven fiber optics dental post including a post body and a woven fiber component. The post body is made of resin material. The post body includes a post face, an irradiation receiving portion, and a bottom. The woven fiber component is provided within the post body. The woven fiber component is formed by intertwining a plurality of fiber optics members. Each fiber optics member has a light receiving end and a light emitting end. A light receiving end portion is composed of the light receiving ends of a plurality of the fiber optics members. A light emitting end portion is composed of the light emitting ends of a plurality of the fiber optics members. The light receiving end portion is appeared on the irradiation receiving portion of the post body for having the woven fiber component receiving a light irradiated at the irradiation receiving portion, and the light emitting end portion is appeared on the post face and/ or the bottom of the post body for having the light received by the woven fiber component transmitting to the light emitting end portion to be emitted out of the post face and/or the bottom.

According to an embodiment of the present invention, the woven fiber component includes a center fiber shaft and a plurality of braided fiber shafts, the center fiber shaft is provided straightly through the woven fiber component, and the plurality of braided fiber shafts is interlaced-knitted around the center fiber shaft.

According to an embodiment of the present invention, it further comprises a bulge ring member bulged from the post body along the radial direction of the post body, and the bulge ring member is made of resin material.

According to an embodiment of the present invention, the woven fiber component is further provided within the bulge ring member.

According to an embodiment of the present invention, the bulge ring member encloses the post body.

According to an embodiment of the present invention, the fiber optics member includes a shell layer and a core layer.

According to an embodiment of the present invention, the coefficient of thermal expansion of the shell layer is lower than the thermal coefficient of thermal expansion of the core layer.

According to an embodiment of the present invention, the refractive index of the shell layer is lower than the refractive index of the core layer.

According to an embodiment of the present invention, the shell layer and the core layer are made of glass.

According to an embodiment of the present invention, the shell layer and the core layer are integrated with each other.

By means of the woven fiber component that is formed by intertwining a plurality of fiber optics member, the woven fiber optics dental post of the present invention has higher structure strength. Furthermore, since the light receiving end portion and the light emitting end portion are respectively composed of a plurality of light receiving ends and light emitting ends of the fiber optics members, the intensity and the uniformity of the light emitted from the woven fiber optics dental post increases, and thus the polymerization of the photocurable adhesive can be more complete so as to shorten the treatment time and to achieve better adhesion efficacy.

BRIEF DESCRIPTION OF THE DRAWINGS

The structure and the technical means adopted by the present invention to achieve the above and other objects can be best understood by referring to the following detailed description of the preferred embodiments and the accompanying drawings. The accompanying drawings and the description are provided for reference only and are not intended to limit the present invention.

FIG. 2A is a top view illustrating the woven fiber optics dental post according to an embodiment of the present invention;

FIG. 2B is a partial top view illustrating the woven fiber optics dental post according to an embodiment of the present invention;

FIGS. 2C and 2D are schematic diagrams illustrating the light emitted from the woven fiber optics dental post according to an embodiment of the present invention;

FIG. 8A is a top view illustrating the woven fiber optics dental post according to another embodiment of the present invention;

FIG. 8B is a partial top view illustrating the woven fiber optics dental post according to another embodiment of the present invention;

FIGS. 8C and 8D are schematic diagrams illustrating the light emitted from the woven fiber optics dental post according to another embodiment of the present invention;

DETAILED DESCRIPTION OF THE PREFERRED EMBODIMENTS

Figures 1, 1A:
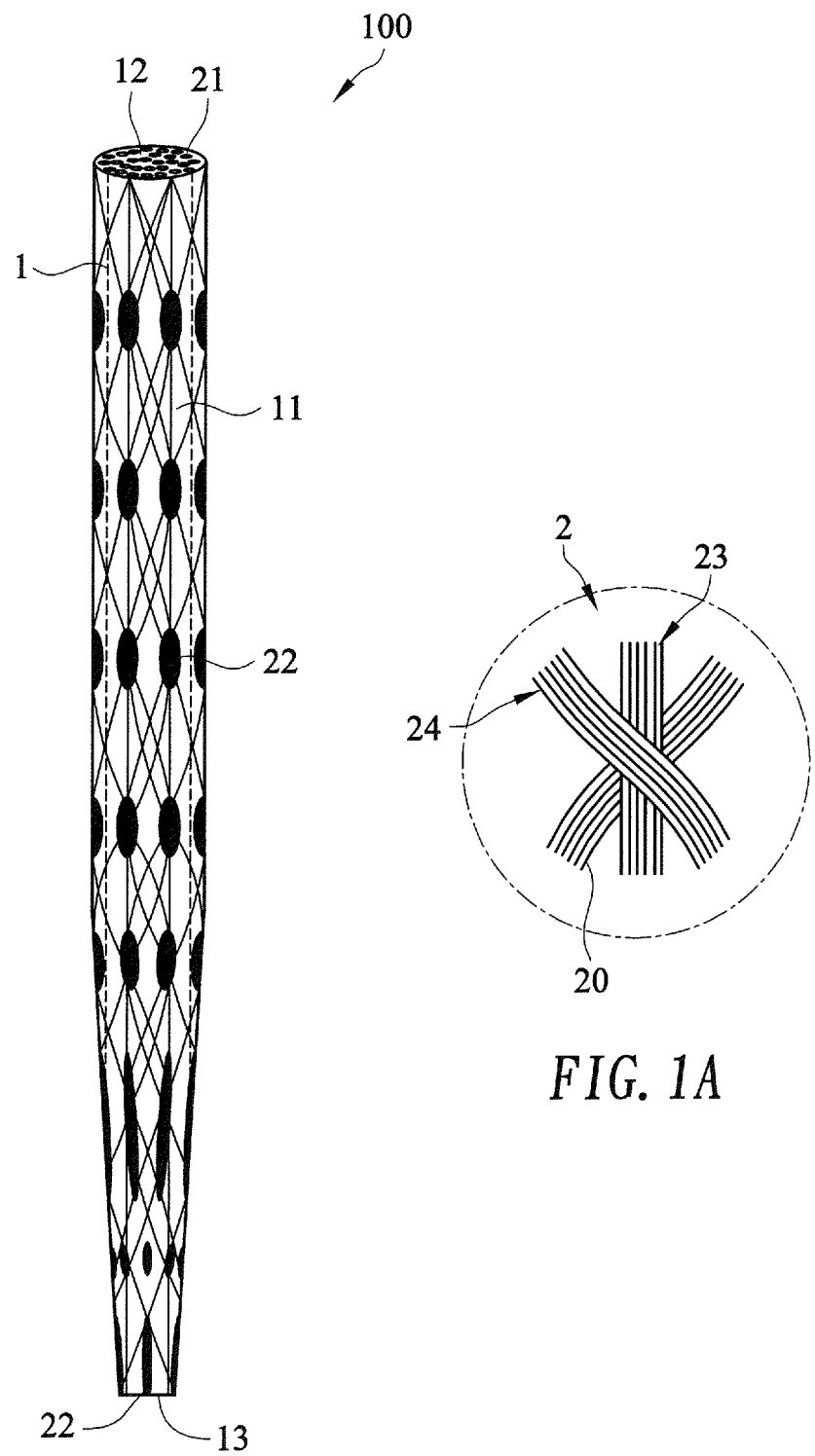
FIG. 1 is a schematic diagram illustrating the woven fiber optics dental post according to an embodiment of the present invention.
FIG. 1A is a schematic diagram illustrating the woven fiber component of the woven fiber optics dental post according to an embodiment of the present invention.

Refer to FIGS. 1 and 1A and FIGS. 2A to 2D. A woven fiber optics dental post 100 according an embodiment of the present invention includes a post body 1 and a woven fiber component 2.

The post body 1 is made of resin material. The post body 1 includes a post face 1, an irradiation receiving portion 12, and a bottom 13.

Figure 9A:
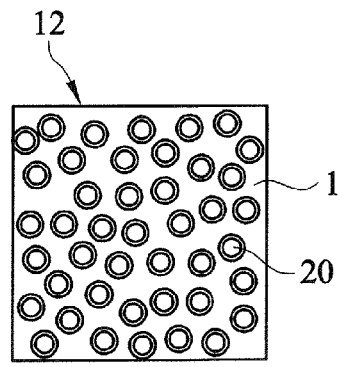
FIGS. 9A to 9D are top views illustrating the post body of the woven fiber optics dental post according to another embodiment of the present invention.
Figure 9B:
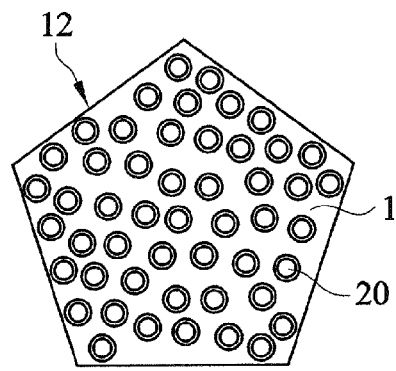
Figure 9C:
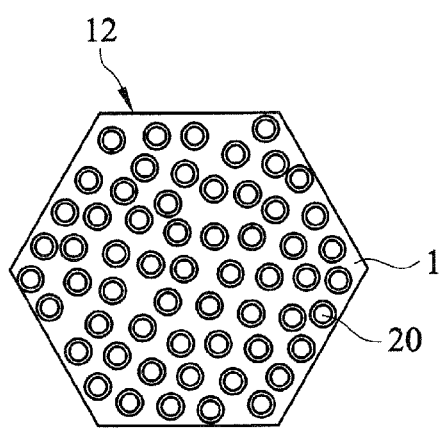
Figure 9D:
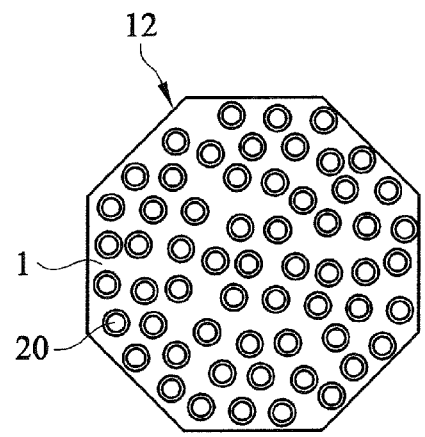

The woven fiber component 2 is provided within the post body 1. The woven fiber component 2 is formed by intertwining a plurality of fiber optics members 20 and thereby is strong so that the woven fiber optics dental post 100 has higher structure strength. Each fiber optics member 20 has a light receiving end and a light emitting end. A light receiving end portion 21 of the woven fiber component 2 is composed of the light receiving ends of a plurality of the fiber optics members 20. A light emitting end portion 22 of the woven fiber component 2 is composed of the light emitting ends of a plurality of the fiber optics members 20. In this embodiment, the woven fiber component 2 includes a center fiber shaft 23 and a plurality of braided fiber shafts 24. The center fiber shaft 23 is provided straightly through the woven fiber component 2. The plurality of braided fiber shafts 24 is interlaced-knitted around the center fiber shaft 23. The center fiber shaft 23 acts as a supporting component that provides an extra fixation for the braided fiber shafts 24, hence tensile strength in the direction of the center fiber shaft increases. Besides, the fiber optics member 20 can be made of materials with Xray opacity, such that the woven fiber optics dental post 100 can be shown up on a Xray scan. In this embodiment, the post body 1 is cylinder-shaped. In other embodiment, the post body 1 can also be rectangular-cylinder-shaped (FIG. 9A), pentagonal-prism-shaped (FIG. 9B), hexagonal-prism-shaped (FIG. 9C), octagon-prism-shaped (FIG. 9D), or other multilateral-prism-shaped, so as to prevent the woven fiber optics dental post 100 in the root canal from being rotated during force application.

As shown in FIGS. 2A to 2D, the light receiving end portion 21 is appeared on the irradiation receiving portion 12 of the post body 1 for having the woven fiber component 2 receiving a light irradiated at the irradiation receiving portion 12. The light emitting end portion 22 is appeared on the post face 12 and the bottom 13 of the post body 1 for having the light received by the woven fiber component 2 transmitting to the light emitting end portion 22 to be emitted out of the post face 11 and the bottom 13, such as light L. Since the light receiving end portion 21 of the woven fiber component 2 is composed of the light receiving ends of a plurality of the fiber optics members 20, and the light emitting end portion 22 of the woven fiber component 2 is composed of the light emitting ends of a plurality of the fiber optics members 20, the intensity of the emitted light L is much higher. In addition, by arranging the light emitting ends of the plurality of fiber optics members 20 with different light-emitting angle, the diffusion of the light L can be more uniform, such that the polymerization of the photocurable adhesive can be more complete. Of course, the present invention is not limited to that, in other embodiment, the light L also can be only emitted from the post face 11 or only emitted from the bottom 13, depending on the position where the light emitting end portion 22 is appeared.

Figure 3A:
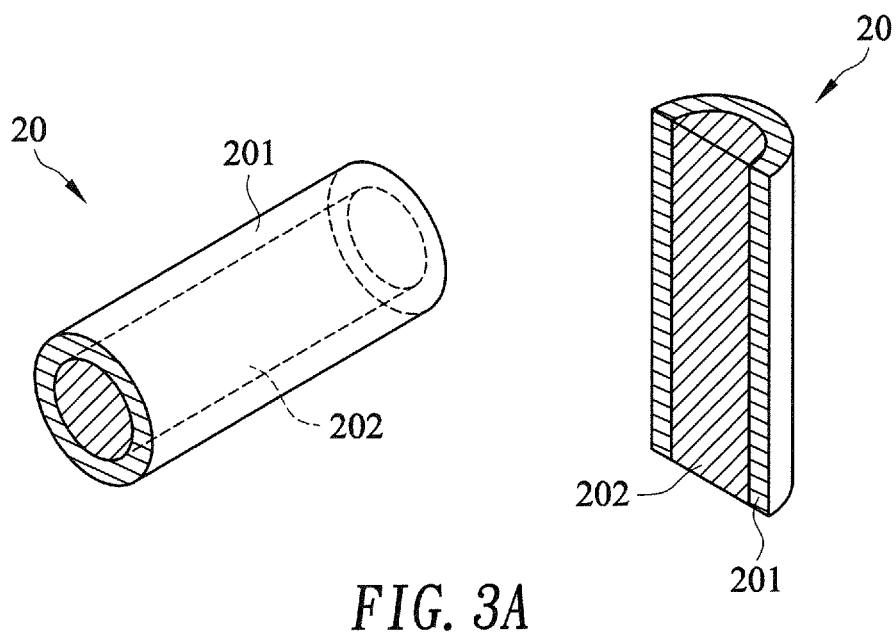
FIG. 3A is a schematic diagram illustrating the fiber optics member of the woven fiber optics dental post according to an embodiment of the present invention.
Figure 3B:
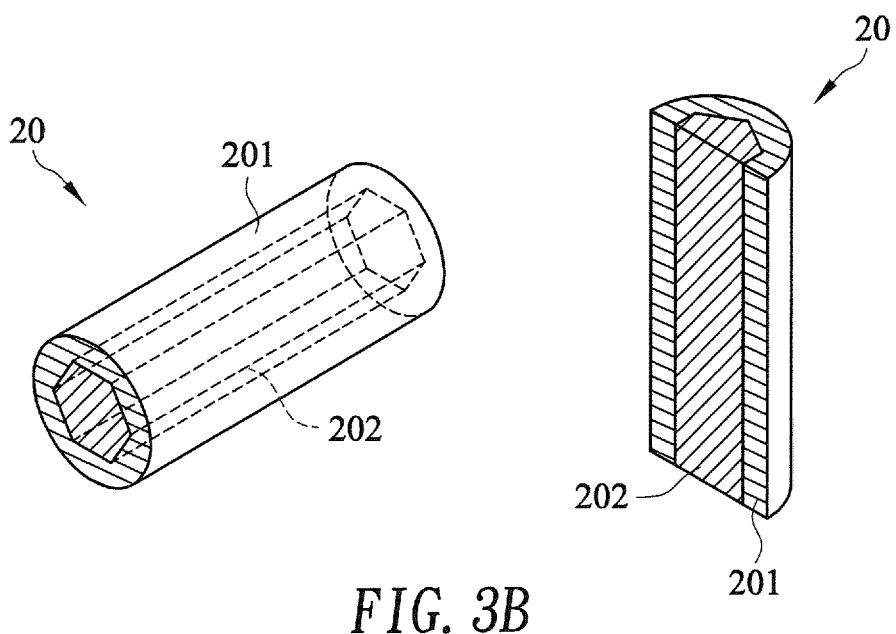
FIG. 3B is a schematic diagram illustrating the fiber optics member of the woven fiber optics dental post according to another embodiment of the present invention.

Refer to FIG. 3A. FIG. 3A shows a fiber optics member 20 according an embodiment of the present invention. In this embodiment, the fiber optics member 20 of the woven fiber optics dental post 100 is a multilayer fiber, and a plurality of coefficients of thermal expansion of layers of the multilayer fiber is gradually lower in order from an inner layer to an outer layer. In this embodiment, the fiber optics member 20 includes a shell layer 201 and a core layer 202. In this embodiment, the shell layer 201 encloses a circumferential surface of the core layer 202 and has a coefficient of thermal expansion lower than that of the core layer 202, and thus higher tensile strength of the fiber optics member 20 can be provided. This configuration is advantageous for the two-layer fiber to be able to provide higher tensile force, and thus higher tensile strength of the woven fiber optics dental post 100 can be provided. Each layer of the multilayer fiber is formed with a round, a hexagonal, or a strip filament. In this embodiment, the shell layer 201 and the core layer 202 are formed with round filaments. In other embodiment, the shell layer 201 is formed with hexagonal filaments, as shown in FIG. 3B. The propose of being formed with hexagonal filaments is to provide the fiber optics member 20 of the woven fiber optics dental post 100 even higher strength. In a preferred embodiment, at least one layer of the fiber optics member 20 is made of materials with Xray opacity, such that the woven fiber optics dental post 100 can be shown up on a Xray scan.

Figure 4A:
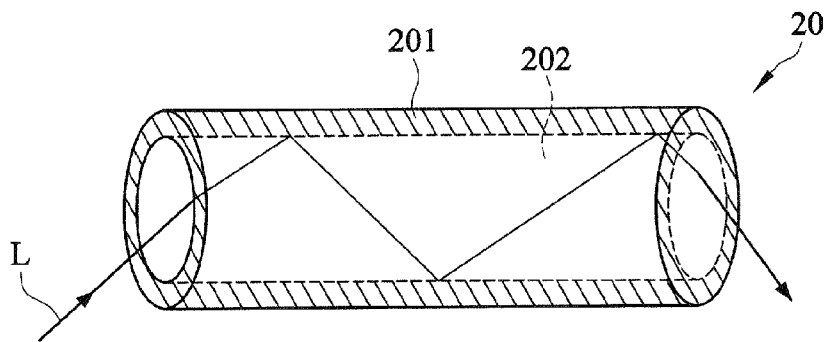
FIG. 4A and FIG. 4B are schematic diagrams illustrating the light emitted from the fiber optics member of the woven fiber optics dental post according to an embodiment of the present invention.
Figure 4B:
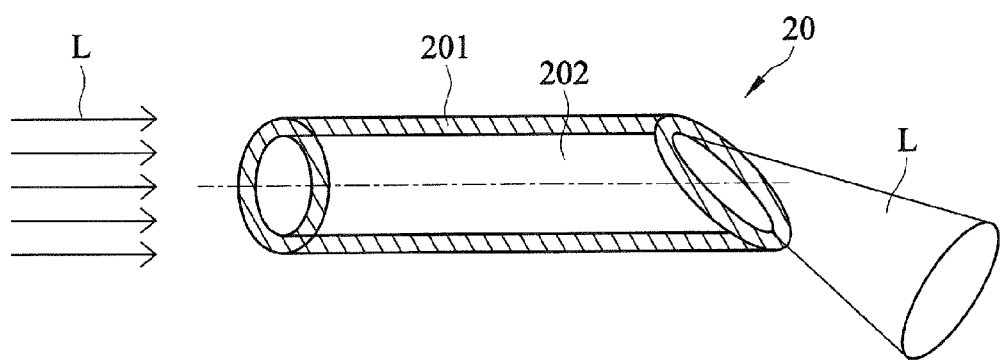
Figure 5A:
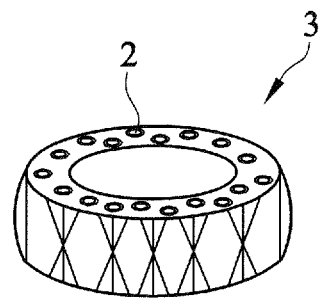
FIG. 5A is a schematic diagram illustrating the bulge ring member of the woven fiber optics dental post according to an embodiment of the present invention.
Figure 5B:
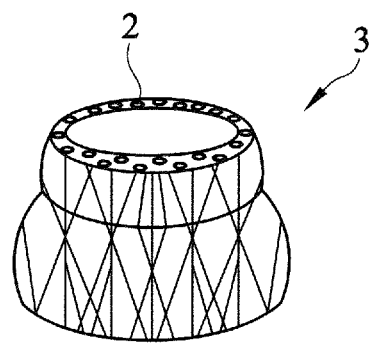
FIG. 5B is a schematic diagram illustrating the bulge ring member of the woven fiber optics dental post according to another embodiment of the present invention.

Refer to FIGS. 4A and 4B. In this embodiment, the refractive index of the shell layer 201 is lower than the refractive index of the core layer 202, so that the light L can be totally reflected along the inside of the core layer 202 to achieve transmission, thus the light L emitted from such light source irradiates into each of the core layer 202 of the fiber optics member 20, and because of the core layer 202 coated with the shell layer 201 with higher refractive index, the light L irradiated inside is transmitted within the core layer 202, so as to achieve the purpose of transmitting the light L by the fiber optics member 20. Preferably, the end of the fiber optics member 20 has an oblique angle relative to the light scattering angle, as shown in FIG. 4B. Preferably, the shell layer 201 and the core layer 202 both are made of optical glass to enhance the numerical aperture, and thus the light scattering angle increases. It further enhances the amount of light receiving and light emitting of the fiber optics member 20, such that the luminous flux of the light L also increases for further enhancing the light intensity of the light L emitted from the light emitting end portion 22 of the woven fiber component 2. Besides, in this embodiment, the shell layer 201 and the core layer 202 are integrated with each other, such that the structure strength of the fiber optics member 20 is enhanced and thus higher tensile strength of the woven fiber optics dental post 100 can be provided.

Figure 6A:
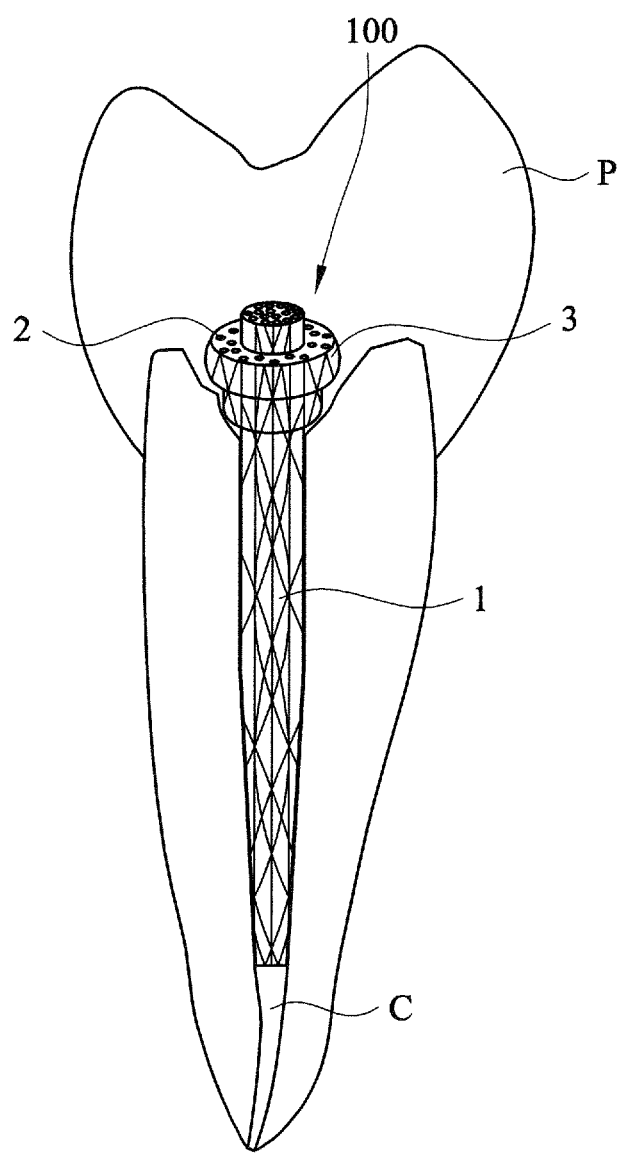
FIGS. 6A to 6C are schematic diagrams illustrating the woven fiber optics dental post used in a root canal according to another embodiment of the present invention.
Figure 6B:
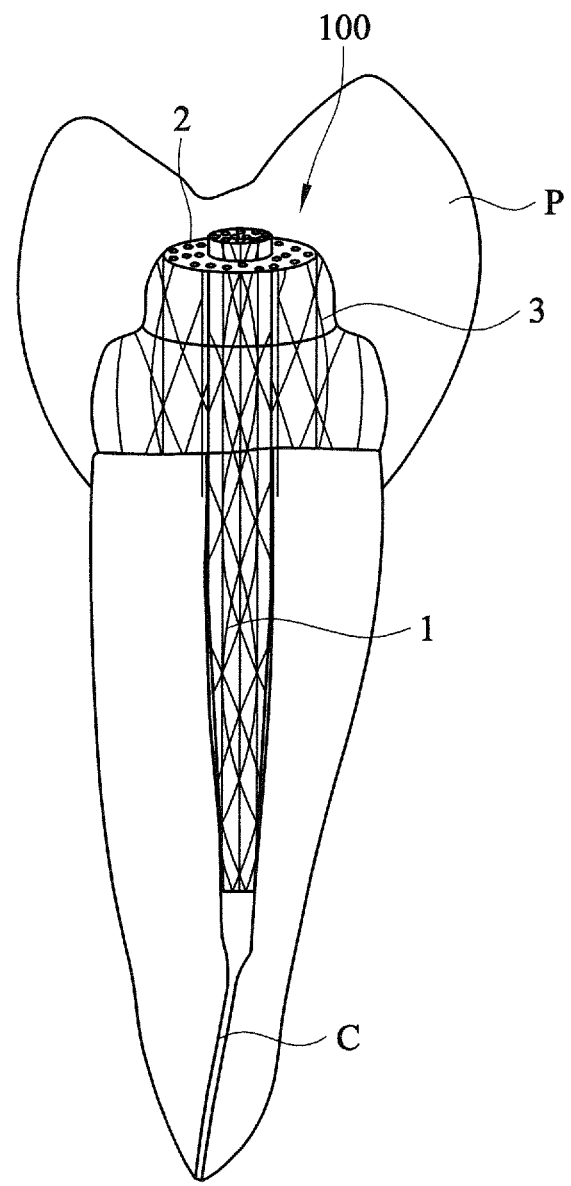
Figure 6C:
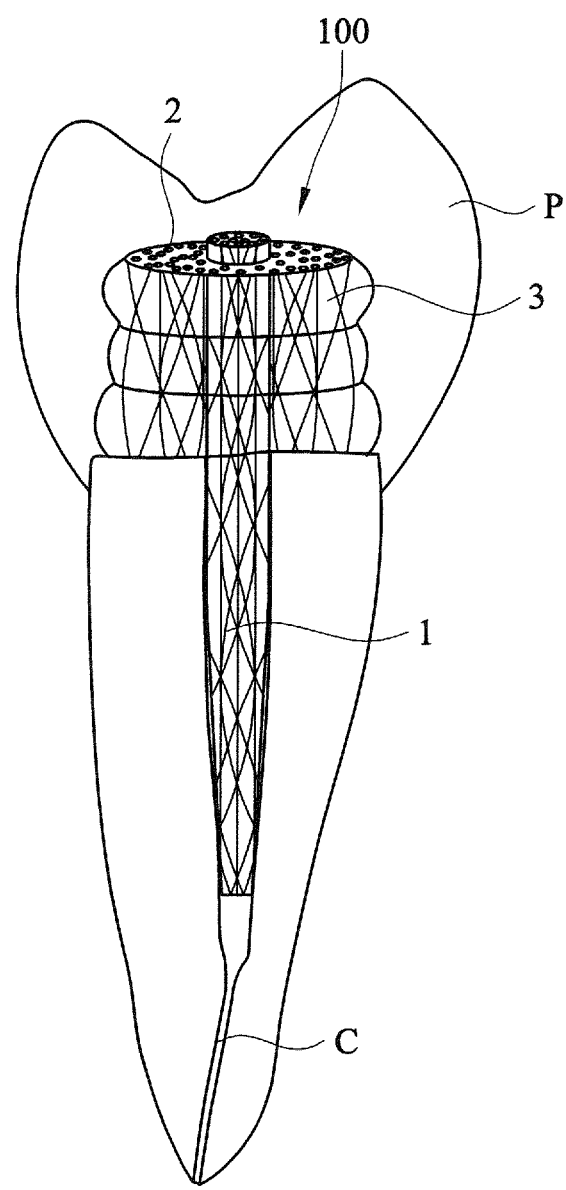
Figure 7A:
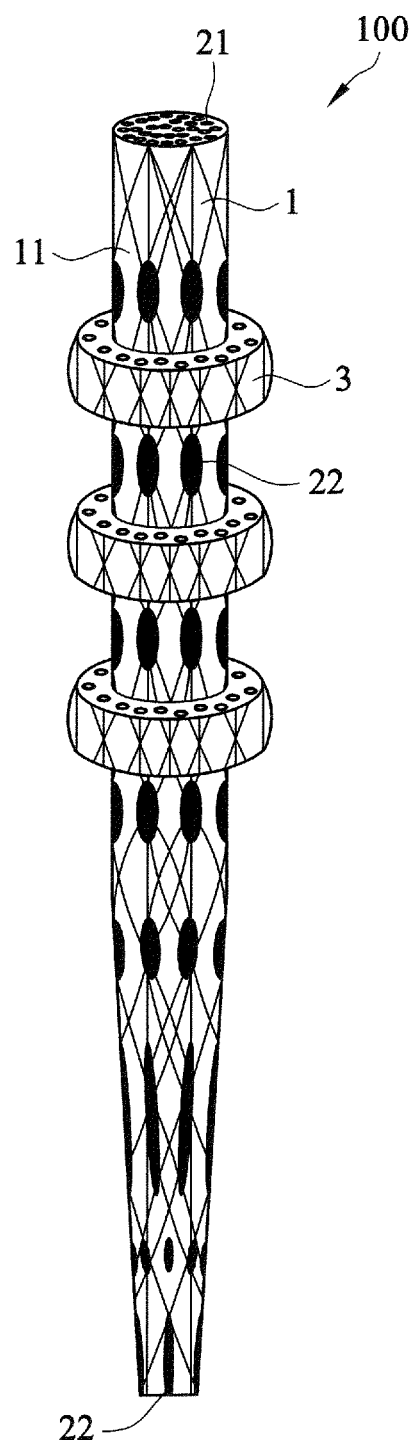
FIGS. 7A to 7C are schematic diagrams illustrating the woven fiber optics dental post according to another embodiment of the present invention.
Figure 7B:
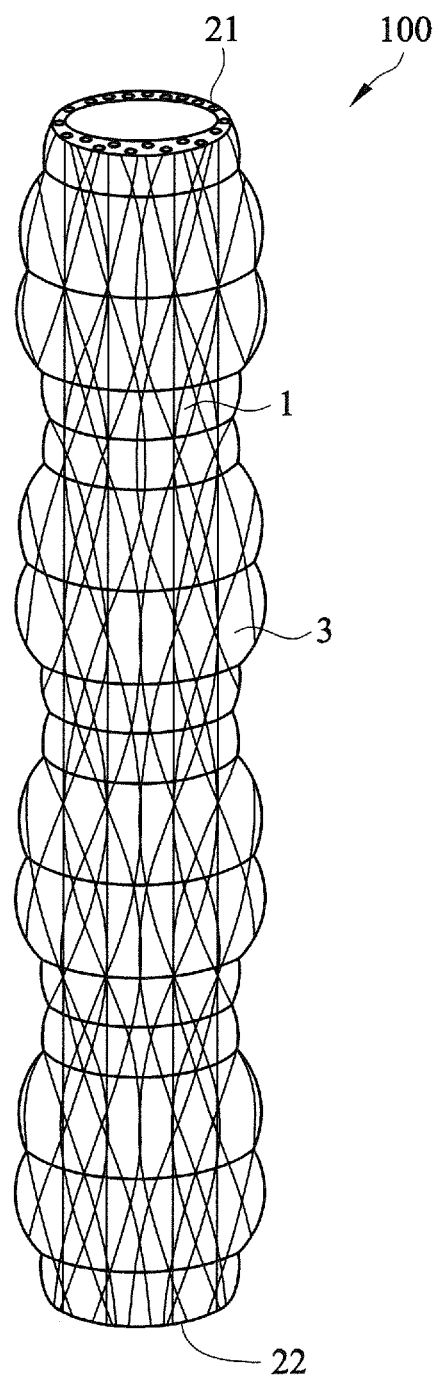
Figure 7C:
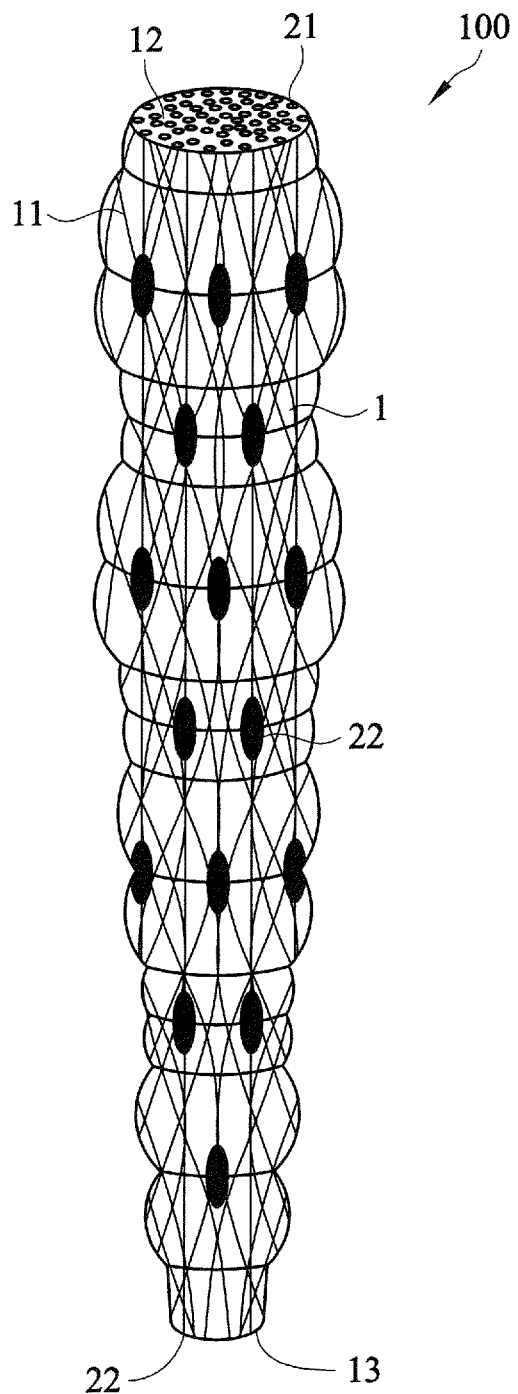
Figure 10A:
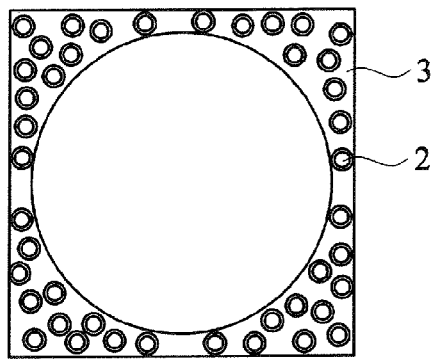
FIGS. 10A to 10D are top views illustrating the bulge ring member of the woven fiber optics dental post according to another embodiment of the present invention.
Figure 10B:
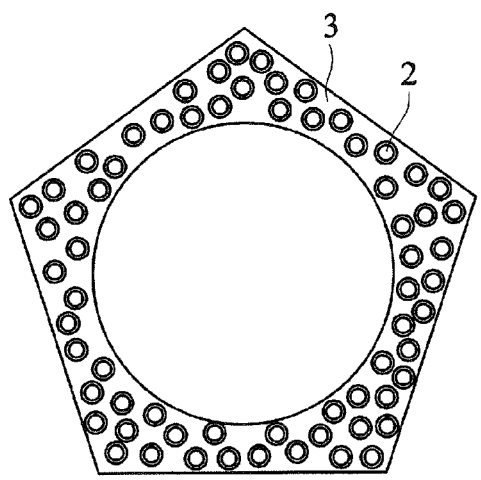
Figure 10C:
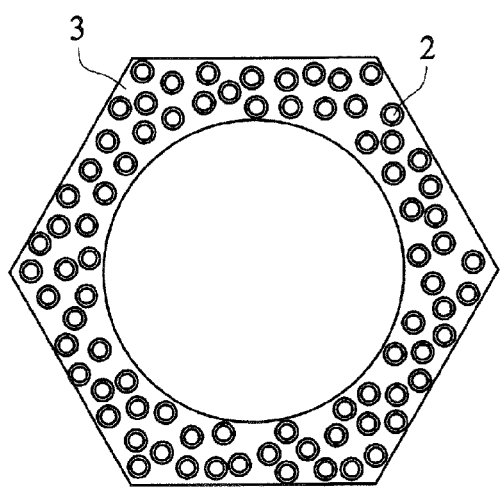
Figure 10D:
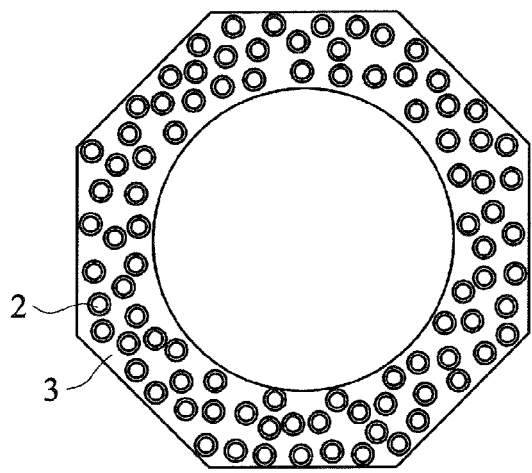

Refer to FIGS. 5A to 5B and FIGS. 6A to 6C. In a preferred embodiment, the woven fiber optics dental post 100 further includes a bulge ring member 3 made of resin material. The bulge ring member 3 is bulged from the post body 1 along the radial direction of the post body 1. The purpose of providing the bulge ring member 3 is to stuff the cavity in a root canal C, as shown in FIG. 6A. FIGS. 8C and 8D are schematic diagrams illustrating the light emitted from the fiber optics member of FIG. 6A. The bulge ring member 3 also can acts as an abutment supporting a dental prosthesis P, as shown in FIGS. 6B to 6C. Preferably, the woven fiber component 2 is further provided within the bulge ring member 3, so that the bulge ring member 3 also can function as the post body 1 in view of light receiving and light emitting to shorten the curing time of photocurable adhesive. In these embodiments, the bulge ring member 3 separably encloses the post body 1. However, the bulge ring member 3 also can be integrated with the post body 1. In addition to the arrangement that the bulge ring member 3 is provided on the top of the post body 1, the bulge ring member 3 also can be provided on the body of the post body 1, as shown in FIG. 7B. In this embodiment, the bulge ring member 3 is hollow-cylinder-shaped. However, the post face 11 of the post body 1 also can be wave-shaped (FIG. 7C) or other irregular-shaped, so as to reduce the possibility that the woven fiber optics dental post 100 in the root canal is loosened, as comparing to the dental post with smooth post face contacting with the root canal. In other embodiment, the bulge ring member 3 can also be hollow-rectangular-cylinder-shaped (FIG. 10A), hollow-pentagonal-prism-shaped (FIG. 10B), hollow-hexagonal-prism-shaped (FIG. 10C), hollow-octagon-prism-shaped (FIG. 10D), or other hollow-multilateral-prism-shaped, so as to prevent the woven fiber optics dental post 100 in the root canal from being rotated during force application.

The above description should be considered as only the discussion of the preferred embodiments of the present invention. However, a person skilled in the art may make various modifications to the present invention. Those modifications still fall within the spirit and scope defined by the appended claims.

We claim:

1. A woven fiber optics dental post, comprising:
a post body made of resin material, the post body including a post face, an irradiation receiving portion, and a bottom; and
a woven fiber component provided within the post body, the woven fiber component being formed by intertwining a plurality of fiber optics members, each fiber optics member having a light receiving end and a light emitting end, a light receiving end portion is composed of the light receiving ends of a plurality of the fiber optics members, a light emitting end portion is composed of the light emitting ends of a plurality of the fiber optics members,
wherein the light receiving end portion is appeared on the irradiation receiving portion of the post body for having the woven fiber component receiving a light irradiated at the irradiation receiving portion, and the light emitting end portion is appeared on the post face and/or the bottom of the post body for having the light received by the woven fiber component transmitting to the light emitting end portion to be emitted out of the post face and/or the bottom;
wherein the woven fiber component comprises a center fiber shaft, which comprises at least one of the plurality of fiber optics members and is provided straightly through the woven fiber component, and a plurality of braided fiber shafts, which each comprises at least one of the plurality of fiber optics members and are interlaced-knitted around the center fiber shaft, such that the center fiber shaft and the plurality of braided fiber shafts are respectively oriented at angular positions to show a pattern that two braided fiber shafts are arranged in an X-shape that crisscrosses the center fiber shaft;
wherein each of the plurality of fiber optics members comprises a shell layer and a core layer, wherein the shell layer encloses a circumferential surface of the core layer and has a coefficient of thermal expansion lower than a coefficient of thermal expansion of the core layer;
wherein the fiber optics members are made of a material with X-ray opacity such that the woven fiber optics dental post is observable with X-ray scanning; and
wherein at least one of the plurality of fiber optics members has an end that forms an oblique angle for varying a light scattering angle of a light beam emitting from the end.

2. The woven fiber optics dental post as claimed in claim 1, further comprising a bulge ring member bulged from the post body along the radial direction of the post body, and the bulge ring member being made of resin material.

3. The woven fiber optics dental post as claimed in claim 2, wherein the woven fiber component is further provided within the bulge ring member.

4. The woven fiber optics dental post as claimed in claim 2, wherein the bulge ring member encloses the post body.

5. The woven fiber optics dental post as claimed in claim 1, wherein the coefficient of thermal expansion of the shell layer is lower than the thermal coefficient of thermal expansion of the core layer.

6. The woven fiber optics dental post as claimed in claim 1, wherein refractive index of the shell layer is lower than the refractive index of the core layer.

7. The woven fiber optics dental post as claimed in claim 1, wherein the shell layer and the core layer are made of glass.

8. The woven fiber optics dental post as claimed in claim 1, wherein the shell layer and the core layer are fused into a single fiber.

* * * * *